United States Patent [19]
Rolf et al.

[11] 4,435,589
[45] Mar. 6, 1984

[54] PROCESS FOR THE PREPARATION OF DIMETHYL SUCCINYLOSUCCINATE, THE DISODIUM SALT THEREOF, DIANILINODIHYDROTEREPHTHALIC ACIDS, THE DIMETHYL ESTERS AND SALTS THEREOF, AND DIANILINOTEREPHTHALIC ACIDS, AND THE DIMETHYL ESTERS AND SALTS THEREOF

[75] Inventors: Meinhard Rolf, Leverkusen; Detlef-Ingo Schütze, Bergisch-Gladbach; Rütger Neeff, Leverkusen; Hans-Volker Runzheimer, Odenthal-Gloebusch, all of Fed. Rep. of Germany

[73] Assignee: Bayer Aktiengesellschaft, Leverkusen, Fed. Rep. of Germany

[21] Appl. No.: 341,047

[22] Filed: Jan. 21, 1982

[30] Foreign Application Priority Data

Feb. 10, 1981 [DE] Fed. Rep. of Germany ....... 3104644

[51] Int. Cl.³ ................. C07C 101/38; C07C 101/68; C07C 103/76
[52] U.S. Cl. ........................ 560/48; 560/21; 560/47; 562/435; 562/456; 562/457
[58] Field of Search .................. 560/126, 48, 21, 47; 562/457, 435, 456

[56] References Cited
U.S. PATENT DOCUMENTS

| 2,782,220 | 2/1957 | Ingram | 560/126 |
| 2,803,644 | 8/1957 | Lemel | 560/126 |
| 2,821,541 | 1/1958 | Struve | 560/48 |
| 3,024,268 | 3/1962 | Struve | 560/126 |
| 3,045,040 | 7/1962 | Deuschel | 560/48 |
| 4,124,768 | 11/1978 | Kirsch et al. | 560/48 X |

FOREIGN PATENT DOCUMENTS

| 891640 | 3/1962 | United Kingdom . |
| 975466 | 11/1964 | United Kingdom . |
| 1228727 | 4/1971 | United Kingdom . |

Primary Examiner—Bernard Helfin
Attorney, Agent, or Firm—Sprung, Horn, Kramer & Woods

[57] ABSTRACT

Process for the preparation of dimethyl succinylosuccinate, or the disodium salt thereof, by condensation of dimethyl succinate in a 35–45 percent by weight solution of sodium methylate in methanol, and a process for the preparation of dianilinodihydroterephthalic acids, the dimethyl esters and salts thereof, and of dianilinoterephthalic acids, and the dimethyl esters and salts thereof, starting from the disodium salt of dimethyl succinylosuccinate prepared according to the new process, without intermediate isolation.

14 Claims, No Drawings

PROCESS FOR THE PREPARATION OF DIMETHYL SUCCINYLOSUCCINATE, THE DISODIUM SALT THEREOF, DIANILINODIHYDROTEREPHTHALIC ACIDS, THE DIMETHYL ESTERS AND SALTS THEREOF, AND DIANILINOTEREPHTHALIC ACIDS, AND THE DIMETHYL ESTERS AND SALTS THEREOF

The invention relates to a process for the preparation of dimethyl succinylosuccinate, the disodium salt thereof, and of dianilinodihydroterephthalic acids, the dimethyl esters and salts thereof, and of dianilinoterephthalic acids, and the dimethyl esters and salts thereof, starting from the disodium salt of dimethyl succinylosuccinate prepared according to the new process, without intermediate isolation. The compounds mentioned, particularly dianilinoterephthalic acids, are important intermediate products for the preparation of valuable violet and red quinacridone pigments.

Processes for the preparation of dimethyl succinylosuccinate and dianilinoterephthalic acids or esters have already been proposed in the literature [see, for example, Ann. 229, 52 (1885); Ann. 404, 272 (1914); U.S. Pat. No. 2,803,644; U.S. Pat. No. 3,024,268; French Patent Specification No. 1,352,663; Japanese Patent Specification No. 50,019-738; Japanese Patent Specification No. 52,059-135; DE-AS (German Published Specification) No. 1,144,285; DE-AS (German Published Specification) No. 1,082,907; DE-AS (German Published Specification) No. 1,328,683; DE-AS (German Published Specification) No. 2,542,494; DE-AS (German Published Specification) No. 1,118,215; and Japanese Patent Specification 9,108,036].

None of the processes known from the literature are completely satisfactory in practice. Thus, dianilinoterephthalic acids are almost always prepared using isolated and dried dialkyl succinylosuccinate as the starting compound. The intermediate drying and isolation require considerable expenditure of time, apparatus, personnel and energy. Although according to DE-AS (German Published Specification) No. 1,082,907 the preparation is carried out as a one-stage process, the dianilinoterephthalate is obtained in a solvent such as dimethylformamide, which is not inert in the subsequent hydrolysis reaction.

Most of the instructions in the literature recommend the use of metallic sodium for the preparation of dimethyl succinylosuccinate.

However, owing to the risk of fire and explosion associated therewith, this procedure can be carried out for a large-scale industrial preparation only with troublesome and expensive safety precautions. Nevertheless, the use of metallic sodium cannot be dispensed with in this process, since the yields are significantly lower when alcoholates are used as bases (see DE-AS (German Published Specification) No. 1,082,907, page 1, line 34–40).

Inert aromatics are mostly used as the solvent, and alcohols are avoided since they are "unsuitable diluents for kinetic reasons" (DE-AS (German Published Specification) No. 1,082,907, page 1, line 48/49) and lead to lower yields. Since 4 mols of methanol are liberated in the condensation of dimethyl succinate to give dimethyl succinylosuccinate, when the condensation is carried out in solvents, mixtures of these solvents with methanol are always obtained during the course of the reaction, the separation of which mixtures is often time-consuming and expensive.

Surprisingly, it has now been found that dimethyl succinylosuccinate can be prepared in good yields in methanol as the solvent and without the use of metallic sodium.

The new process for the preparation of dimethyl succinylosuccinate or the disodium salt thereof is characterised in that dimethyl succinate is condensed in a 35–45 percent by weight solution of sodium methylate in methanol.

The reaction proceeds according to

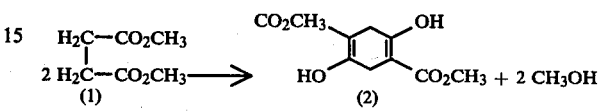

The process is preferably carried out as follows:

Dimethyl succinate is added to a 35–45 percent by weight solution of 120–180%, preferably 140–160% of theory sodium methylate in methanol at 80°–120° C., preferably at 90°–100° C., and if appropriate under pressure, a part of the methanol is distilled off and the mixture is boiled, if appropriate, for a further 6–12 hours in a reflux condenser. If desired, the disodium salt can be isolated at this point in a manner which is in itself known. By means of an excess of an inorganic or organic acid, for example aqueous sulphuric acid, phosphoric acid, hydrochloric acid, acetic acid or formic acid, dimethyl succinylosuccinate can be liberated from the disodium salt, without isolation or after isolation from the reaction mixture, and can be isolated in good yield by filtration.

The process, according to the invention, for the preparation of dimethyl dianilinodihydroterephthalate of the formula

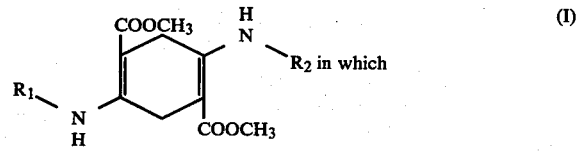

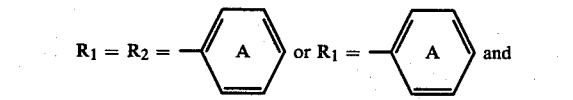

it being possible for the rings A and B to be substituted by 1 to 4 substituents from the series comprising $C_1$–$C_4$-alkyl, chlorine, fluorine, $C_1$–$C_4$-alkoxy, carbamoyl which is optionally monosubstituted or disubstituted by $C_1$–$C_4$-alkyl, trifluoromethyl, carboxyl or nitro, or it being possible for an aromatic or heteroaromatic ring to be fused to them, or dianilinodihydroterephthalic acids or the salts thereof, is characterised in that the suspension of the disodium salt of dimethyl succinylosuccinate, which suspension is obtained by condensation of dimethyl succinate in a 35–45 percent by weight solution of sodium methylate in methanol, is acidified, and the liberated dimethyl succinylosuccinate is condensed with at least 2 mols of a compound of the formula

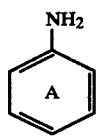
(II)

in which

A has the meaning given under formula (I), or with, altogether, at least 2 mols of a mixture of a compound of the formula (II) and a compound, which differs therefrom, of the formula (III)

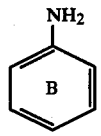
(III)

in which

B has the meaning given under formula (I), or with salts of the amines (III) and/or (II) with inorganic or organic acids.

The resulting dimethyl ester can be hydrolysed in a customary manner in an alkaline medium and the dicarboxylic acids can be liberated by the addition of acid. If desired, the dimethyl ester, the alkali metal salts formed by the hydrolysis and the dicarboxylic acids can be isolated in a manner which is in itself known. These compounds can be employed as starting materials for the synthesis of special quinacridones by first subjecting them to cyclisation and then oxidising the product to give the pigment.

However, the dimethyl esters of the formula (I) are preferably further processed without intermediate isolation to give optionally substituted dianilinoterephthalic acids of the formula (IV)

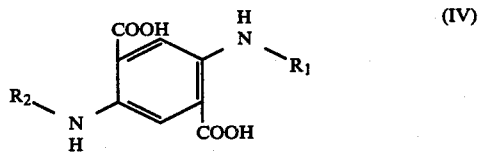
(IV)

in which $R_1$ and $R_2$ have the meanings given under formula (I), or dimethyl esters and salts of the dicarboxylic acids of the formula (IV).

For this purpose, the suspension of the esters of dianilinodihydroterephthalic acid obtained in the manner indicated above is oxidised to the dimethyl esters of the compounds of the formula (IV), which are hydrolysed in an alkaline medium to give the salts of the dianilinoterephthalic acids of the formula (IV); the free dicarboxylic acids (IV) can be liberated by the addition of acid and can be isolated in a manner which is in itself known. If desired, the dimethyl esters and salts of the compounds of the formula (IV) can also be isolated in a customary manner.

Aniline, p-toluidine or p-chloroaniline are preferably employed as amines of the formula (II) and (III); the reaction is particularly preferably carried out using only one amine.

In a preferred embodiment, the suspension of the disodium salt of dimethyl succinylosuccinate is acidified, for example with sulphuric acid, hydrochloric acid, phosphoric acid, acetic acid, formic acid or carbonic acid, 110–200% of a compound of the formula (II) or a mixture of two compounds of the formula (II) and (III) is then added, it also being possible for the amines to be present completely or partially in the form of their salts with the abovementioned acids, and the mixture is stirred at 90°–130° C. until the reaction is complete. The suspension thus obtained, of the ester of the formula (I), is then rendered alkaline, without isolation, and is oxidised at 60°–120° C., if appropriate under pressure. The preferred oxidising agent is air, but nitroaromatics, such as m-nitrobenzenesulphonic acid or nitro compounds of the formula

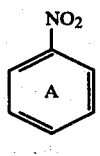

in which the ring A' can carry 1 to 4 substituents from the series comprising $C_1$–$C_4$-alkyl, chlorine, fluorine, $C_1$–$C_4$-alkoxy, carbamoyl which is optionally monosubstituted or disubstituted by $C_1$–$C_4$-alkyl, trifluoromethyl, carboxyl or nitro, or an aromatic or heterocyclic ring can be fused to it, also give very good results.

0.5 to 5% (relative to material to be oxidised) of quinones, such as anthraquinone, phenanthraquinone, naphthoquinone and chloranil, and the sulphonic acids and carboxylic acids thereof, are preferably employed as oxygen carriers in the case of oxidation by air. The use of anthraquinonemonosulphonic acids and anthraquinonedisulphonic acids, particularly anthraquinone-2-sulphonic acid, is preferred.

In most of the cases, the hydrolysis to the dicarboxylic acid is already effected simultaneously with the oxidation. For completion of the reaction, the temperature can be increased to 80°–150° C., if appropriate under pressure, and the quantity of alkali—preferably sodium hydroxide or potassium hydroxide—can be increased. If appropriate, phase-transfer catalysts can be added in addition.

THe dicarboxylic acid can be liberated from the dialkali metal salt suspension which is present, by means of an excess of the abovementioned acids, if appropriate after dilution with water and a clarifying filtration, and can be isolated by filtration.

The process according to the invention yields the dianilinoterephthalic acids in good yields and in very hgh purities. They can be reacted without further purification, for example according to the process mentioned in U.S. Pat. No. 3,342,823, to give quinacridone pigments.

EXAMPLE 1

234 g of dimethyl succinate are added dropwise to 350 g of a 37% strength sodium methylate solution in methanol at 95°–100° C., under nitrogen. 220 ml of methanol are then distilled off at the same temperature and the mixture is boiled for a further 6 hours in a reflux condenser. The reaction mixture is then acidified by introducing a mixture of 1.2 kg of ice and 120 ml of concentrated sulphuric acid and is filtered under suction at room temperature, and the residue is washed with water until the runnings are neutral. 139 g (76% of theory) of dimethyl succinylosuccinate of melting point 154°–155° C. remain after the drying process.

EXAMPLE 2

234 g of dimethyl succinate are added dropwise to 350 g of a 37% strength sodium methylate solution in methanol at 95°–100° C., under nitrogen. 220 ml of methanol are then distilled off at the same temperature and the mixture is boiled for a further 6 hours in a reflux condenser. 80 g of methanol and 200 g of glacial acetic acid are then added to the methanolic distillate and the mixture is stirred until it is homogeneous. After 143 g of aniline have been added, the mixture is stirred under pressure at 105° for 2 hours, 3 g of anthraquinone-2-sulphonic acid and 500 g of 30% strength sodium hydroxide solution are then added to it at room temperature, and air is blown through the mixture at approx. 70°, whilst stirring well, until a sample dissolves completely when diluted with water. 2 l of water are added to the mixture, the latter is filtered through whilst hot and the filtrate is acidified with approx. 500 g of concentrated sulphuric acid. After the mixture has been filtered under suction and the residue has been washed with hot water and dried at 70° C., 210 g (75%) of dianilinoterephthalic acid of the formula

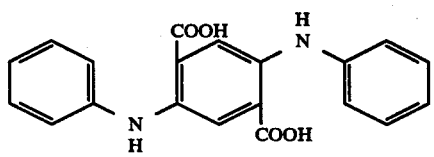

remain.

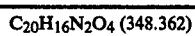

| $C_{20}H_{16}N_2O_4$ (348.362) | | | |
|---|---|---|---|
| calculated | C: 68.96 | H: 4.63 | N: 8.04 |
| found | C: 69.0 | H: 4.5 | N: 8.1 |

EXAMPLE 2a

The dianilinoterephthalic acid is obtained in equally good quality and yield if the addition of anthraquinone-2-sulphonic acid and the passage of air through the mixture are dispensed with, and the mixture is oxidised, instead, with 132 g of m-nitrobenzenesulphonic acid (Na salt).

EXAMPLE 3

When 200 g of p-chloroaniline are employed instead of 143 g of aniline, 240 g (72% of theory) of the dichloroanilinoterephthalic acid of the formula

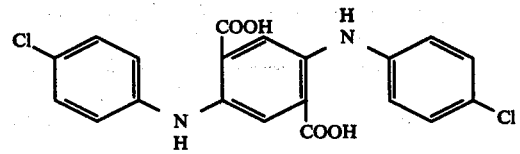

are obtained according to the process described in Example 2.

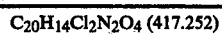

| $C_{20}H_{14}Cl_2N_2O_4$ (417.252) | | | |
|---|---|---|---|
| calculated | C: 57.57 | H: 3.38 | N: 6.71 |
| found | C: 57.4 | H: 3.4 | N: 6.7 |

EXAMPLE 3a

Dichlorodianilinoterephthalic acid is obtained in a similar yield and quality if the oxidation is carried out using m-nitrobenzenesulphonic acid instead of air.

EXAMPLE 4

When 165 g of p-toluidine are employed instead of 143 g of aniline, 226 g (75.1%) of the ditoluidinoterephthalic acid of the formula

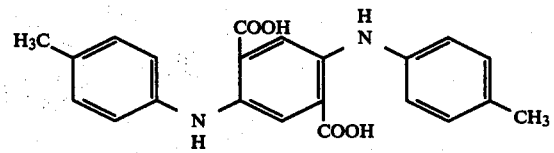

are obtained according to the process described in Example 2.

| $C_{22}H_{20}N_2O_4$ (376.416) | | | |
|---|---|---|---|
| calculated | C: 70.20 | H: 5.36 | N: 7.44 |
| found | C: 70.2 | H: 5.3 | N: 7.5 |

EXAMPLE 4a

Ditoluidinoterephthalic acid is obtained in a similar yield and quality if the oxidation is carried out using m-nitrobenzenesulphonic acid instead of air.

Using, instead of aniline, the anilines listed in the following table, the corresponding dianilinoterephthalic acids are obtained in very good purities, according to the process mentioned in Example 1a. The elementary analyses of the individual products agreed well with the calculated values.

| Example | Aniline | Dianilinoterephthalic acid |
|---|---|---|
| 5 | ![NH2-C6H4-CF3] | ![structure with CF3 groups] |

| Example | Aniline | Dianilinoterephthalic acid |
|---|---|---|
| 6 | 4-fluoroaniline | bis(4-fluoroanilino)terephthalic acid |
| 7 | 4-(N,N-dimethylcarbamoyl)aniline | bis[4-(N,N-dimethylcarbamoyl)anilino]terephthalic acid |
| 8 | 1-naphthylamine | bis(1-naphthylamino)terephthalic acid |
| 9 | 4-methoxyaniline | bis(4-methoxyanilino)terephthalic acid |
| 10 | 3,4-dichloroaniline | bis(3,4-dichloroanilino)terephthalic acid |
| 11 | aniline + 4-chloroaniline (1:1) | dianilino (approx. 25%); anilino-4-chloroanilino (approx. 50%); bis(4-chloroanilino) (approx. 25%) |

We claim:

1. Process for the preparation of dimethyl succinylosuccinate or the disodium salt thereof, characterized in that dimethyl succinate is condensed in a 35–45 percent by weight solution of 120–180 percent of theory sodium methylate in methanol and the disodium salt is isolated or dimethyl succinylosuccinate is liberated by means of an acid and is isolated.

2. Process for the preparation of dimethyl dianilinodihydroterephthalates of the formula (I),

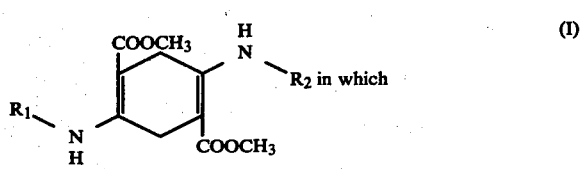

in which

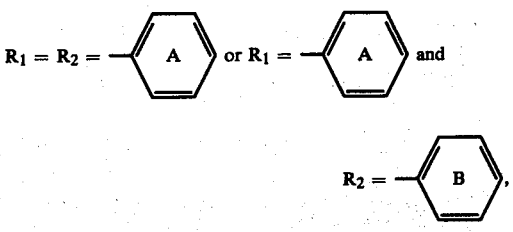

the rings A and B optionally being substituted by 1 to 4 substituents from the group comprising $C_1$–$C_4$-alkyl, chlorine, fluorine, $C_1$–$C_4$-alkoxy, carbamoyl which is optionally monosubstituted or disubstituted by $C_1$–$C_4$-alkyl, trifluoromethyl, carboxyl or nitro, or optionally an aromatic ring is fused thereto, characterized in that the suspension of the disodium salt of dimethyl succinylosuccinate, which suspension is obtained by condensation of dimethyl succinate in a 35–45 percent by weight solution of 120–180 percent of theory of sodium methylate in methanol, is acidified, the liberated dimethyl succinylosuccinate is condensed with at least two mols of a compound of the formula

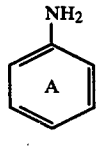 (II)

in which

A has the meaning given under formula (I), or with, altogether, at least 2 mols of a mixture of a compound of the formula (II) and a compound, which differs therefom, of the formula (III)

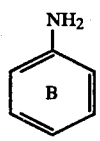 (III)

in which B has the meaning given under formula (I), or with salts of the amines (III) and/or (II), and the dimethyl esters are isolated.

3. Process according to claim 2, characterised in that the reaction is carried out using at least two mols of aniline, p-toluidine and/or p-chloroaniline.

4. Process for the preparation of dianilinodihydroterephthalic acids or the salts thereof, characterised in that the dimethyl esters obtained according to the process of claims 2 or 3 are hydrolysed in alkaline medium, without intermediate isolation, or the dicarboxylic acids are liberated from them without intermediate isolation and these acids are isolated.

5. Process for the preparation of dianilinoterephthalic acids of the formula

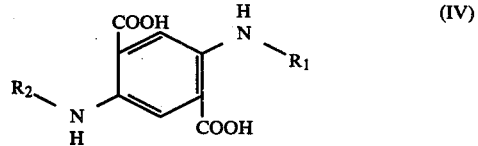

in which $R_1$ and $R_2$ have the meanings given under formula (I), characterised in that the dimethyl esters of dianilinodihydroterephthalic acid obtained according to the processes of claims 2 and 3 are oxidised, the resulting dimethyl esters of dianilinoterephthalic acids are hydrolysed in an alkaline medium to give the salts of the dianilinoterephthalic acids, and the free acids of the formula (IV) are liberated by the addition of acid and are isolated.

6. Process according to claim 5, characterised in that the dimethyl esters of the dianilinodihydroterephthalic acids are oxidised using air.

7. Process for the preparation of the dimethyl esters of dianilinoterephthalic acids of the formula (IV), characterised in that these esters are isolated, during the course of the process according to claims 5 or 6.

8. Process for the preparation of the salts of dianilinoterephthalic acids of the formula (IV), characterised in that these salts are isolated, during the course of the processes according to claims 5 or 6.

9. A process according to claim 1 wherein said sodium methylate is employed in an amount of 140–160 percent of theory.

10. A process according to claim 2 wherein said sodium methylate is employed in an amount of 140–160 percent of theory.

11. A process according to claim 4 wherein dicarboxylic acid salts are isolated.

12. A process according to claim 4 wherein dicarboxylic acid is isolated.

13. A process according to claim 1 when the process is carried out at a temperature of 80°–120° C.

14. A process according to claim 2 when the condensation with sodium methylate is carried out at a temperature of 80°–120° C.

* * * * *